(12) United States Patent
McGurk

(10) Patent No.: US 7,291,130 B2
(45) Date of Patent: Nov. 6, 2007

(54) SAFETY NEEDLE AND CATHETER ASSEMBLY

(75) Inventor: Joseph P. McGurk, Mason, OH (US)

(73) Assignee: Smiths Medical ASD, Inc., Keene, NH (US)

( * ) Notice: Subject to any disclaimer, the term of this patent is extended or adjusted under 35 U.S.C. 154(b) by 359 days.

(21) Appl. No.: 10/713,917

(22) Filed: Apr. 8, 2003

(65) Prior Publication Data
US 2004/0243061 A1 Dec. 2, 2004

(51) Int. Cl.
*A61M 5/178* (2006.01)
(52) U.S. Cl. .................. 604/164.08; 604/110
(58) Field of Classification Search ........... 604/164.08
See application file for complete search history.

(56) References Cited

U.S. PATENT DOCUMENTS

| | | | | |
|---|---|---|---|---|
| 3,520,292 | A * | 7/1970 | Barr, Jr. et al. ............. | 600/577 |
| 4,013,080 | A | 3/1977 | Froning ...................... | 128/347 |
| 5,085,648 | A | 2/1992 | Purdy | |
| 5,120,321 | A | 6/1992 | Oksman et al. ............. | 604/198 |
| 6,261,259 | B1 * | 7/2001 | Bell .......................... | 604/93.01 |
| 6,287,278 | B1 * | 9/2001 | Woehr et al. ............... | 604/110 |
| 6,402,734 | B1 | 6/2002 | Weiss ......................... | 604/521 |
| 6,585,704 | B2 * | 7/2003 | Luther et al. ............... | 604/263 |
| 6,629,959 | B2 | 10/2003 | Kuracina et al. | |
| 6,749,588 | B1 | 6/2004 | Howell et al. ......... | 604/164.08 |
| 2002/0004650 | A1 | 1/2002 | Kuracina et al. | |
| 2002/0103463 | A1 * | 8/2002 | Luther et al. ............... | 604/263 |
| 2002/0177818 | A1 | 11/2002 | Vaillancourt | |
| 2003/0060771 | A1 * | 3/2003 | Bialecki et al. .......... | 604/164.08 |

FOREIGN PATENT DOCUMENTS

| | | |
|---|---|---|
| EP | 0 747 086 A2 | 11/1996 |
| EP | 1 112 754 A1 | 4/2001 |
| WO | WO94/23778 | 10/1994 |
| WO | WO99/08742 | 2/1999 |

OTHER PUBLICATIONS

International Search Report corresponding to International Application No. PCT/US2004/006017 mailed Jul. 16, 2004.

\* cited by examiner

*Primary Examiner*—Nicholas D. Lucchesi
*Assistant Examiner*—Laura Bouchelle
(74) *Attorney, Agent, or Firm*—Wood, Herron & Evans, LLP

(57) ABSTRACT

A catheter and introducer needle assembly having a needle with a proximal and distal end attached to a needle hub and a bent area therebetween. The device further includes a tubular catheter having proximal and distal ends in which the introducer needle can be coaxially received within the catheter. The device has a hollow catheter hub having a distal end attached to the proximal end of the catheter and is in fluid communication therewith. The assembly includes a needle tip protector having a proximal end and a distal end disposed within the catheter hub. The distal end of the protector covers the needle tip when the needle is removed from the catheter. The protector has a proximal opening at its proximal end wherein the bent area is angled away from the proximal opening such that when the needle is removed from the catheter the protector remains attached to the needle.

14 Claims, 8 Drawing Sheets

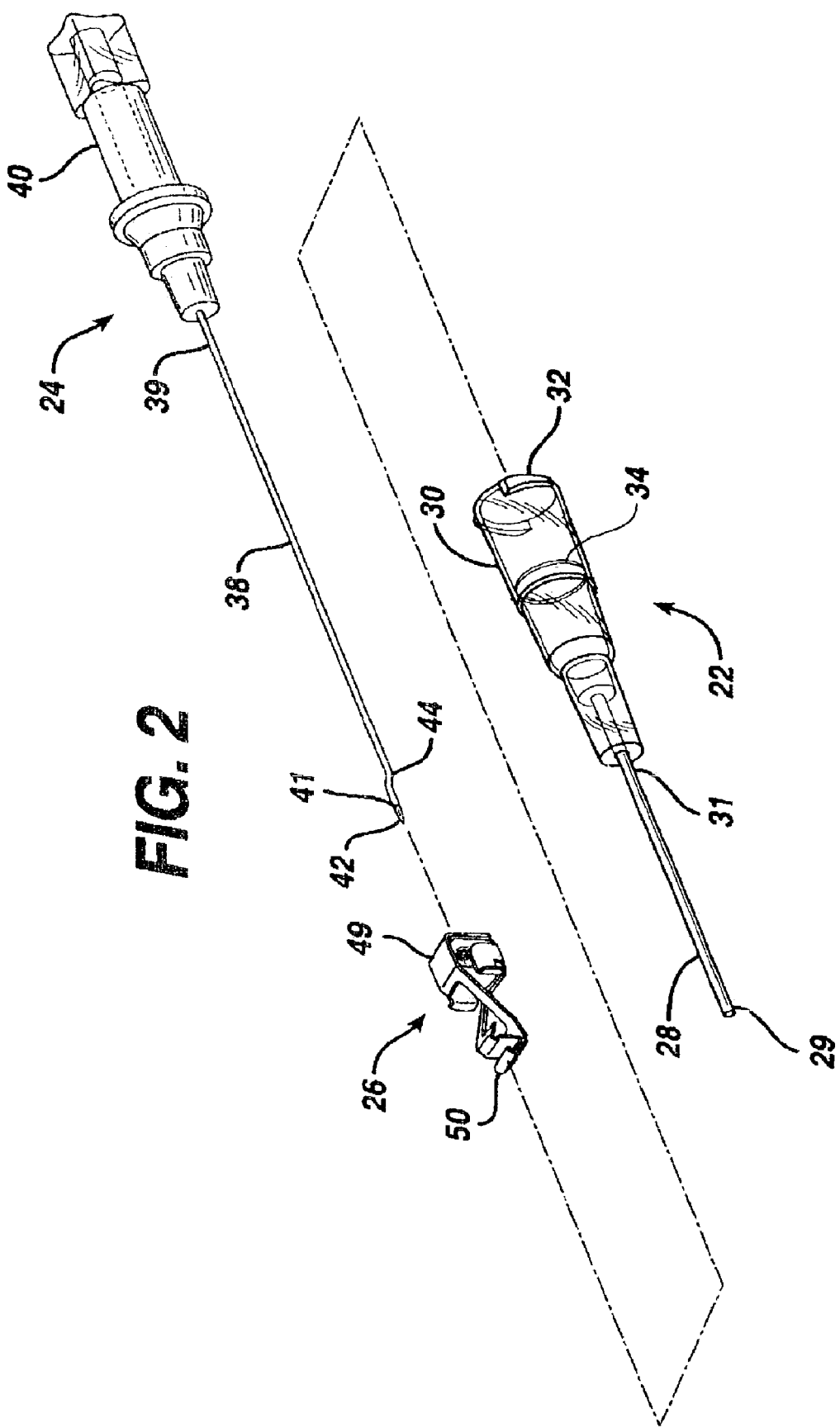

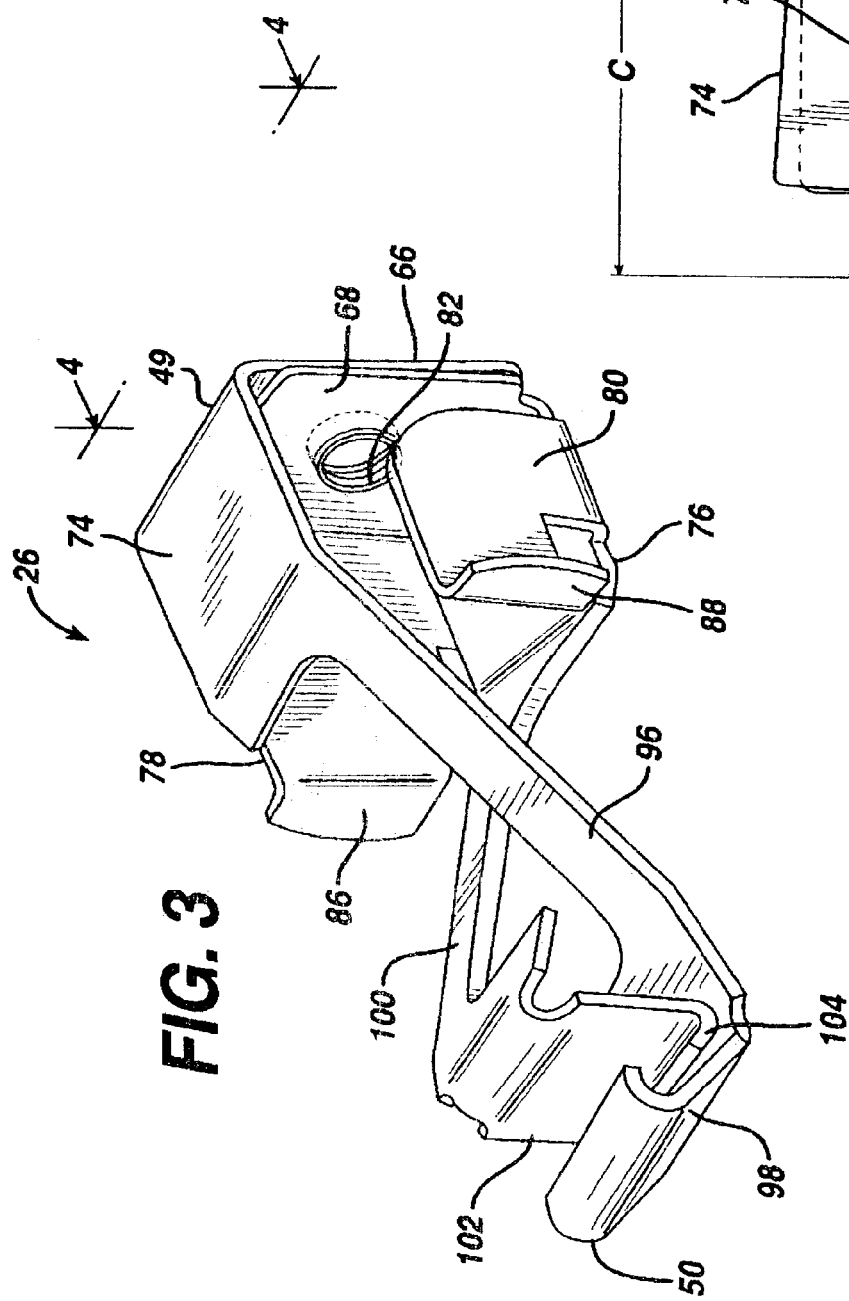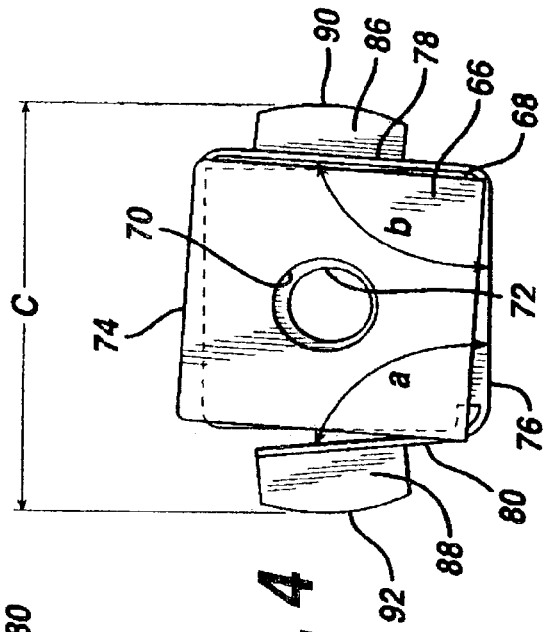

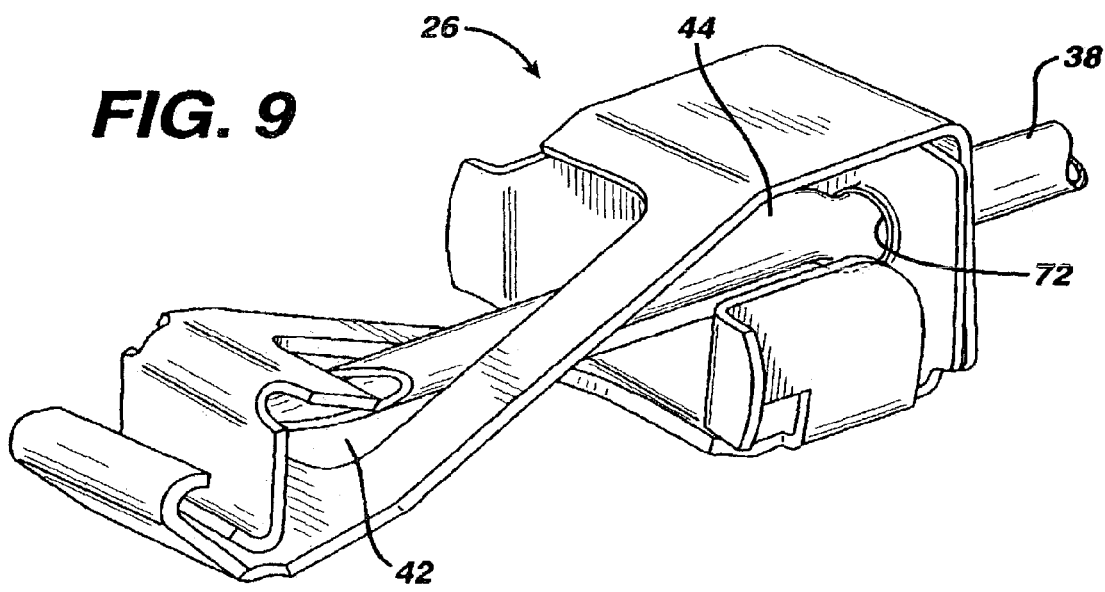

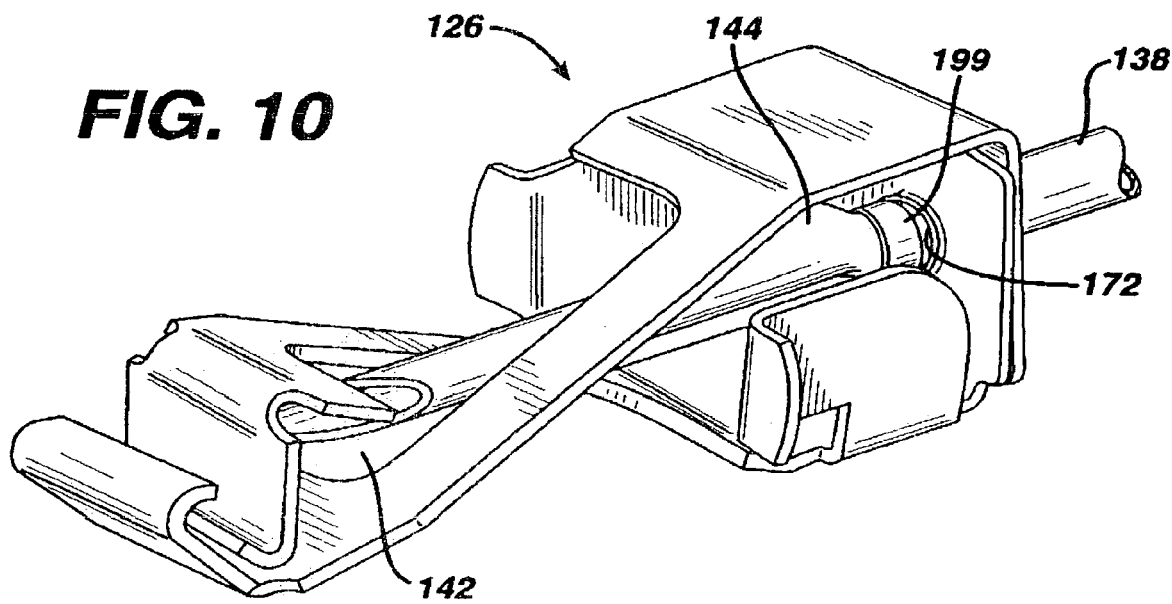

SAFETY NEEDLE AND CATHETER ASSEMBLY

FIELD OF THE INVENTION

The present invention relates, in general, to intravenous (IV) catheters and, more particularly, to a safety IV catheter with a needle tip protector that will automatically cover the needle tip upon needle withdrawal.

BACKGROUND OF THE INVENTION

An intravenous (IV) catheter is an instrument that is used to introduce certain fluids such as saline solution directly into the bloodstream of a patient. Typically, a needle or other stylet is first introduced through the cannula portion of the catheter and into the skin of the patient at the desired location such as the back of the patient's hand or a vessel on the inside of the arm. Once insertion is complete, the needle is removed from the cannula portion of the catheter. After removing the needle, a fluid handling device such as a syringe is attached to the luer fitting located at the proximal end of the catheter hub. Fluid then flows directly from the fluid handling device through the catheter into the bloodstream of the patient.

When the needle is removed from the cannula, the health care worker must place the exposed needle tip at a nearby location while simultaneously addressing the task required to accomplish the needle removal. It is at this juncture that the exposed needle tip creates a danger of an accidental needle stick occurring which leaves the health care worker vulnerable to the transmission of various, dangerous bloodborne pathogens such as human immune virus (HIV) and hepatitis.

The risk of a contaminated needle stick is not just isolated to the health care worker inserting the intravenous catheter. Careless disposal of used needles can put other health care workers at risk as well. Even others outside the health care profession, for example those involved in the clean-up and final disposal of medical waste, are at risk of an accidental needle stick from a carelessly discarded needle.

The danger to health care workers and others outside the health care profession from accidental needle sticks has yielded the development of catheters with safety mechanisms in which the occurrence of such accidental needle sticks is prevented. An example of a catheter having a safety mechanism is disclosed in U.S. Pat. No. Re. 34,416 issued to Lemieux. A safety catheter is described which includes an element that covers the needle tip upon removal of the needle from the catheter. The safety element includes a split flange at its proximal end which is expanded by the needle as the needle is inserted into an undersized hole at the center of this flange. The safety element is thus held secure within the catheter hub by inserting the needle through the undersized hole which forces the outside perimeter of the split flange against the inside wall of the catheter hub. One of the drawbacks to this design is the amount of friction force exerted against the needle by the split flange. A tight fit of the flange against the catheter wall causes great friction against the needle making it difficult to be withdrawn from the catheter by the clinician. A lose fit leaves the flange prone to releasing prematurely from the catheter as the needle is withdrawn, creating the potential that the needle tip will be left exposed.

Another example of a catheter having a safety mechanism is disclosed in U.S. Pat. No. 6,117,108 issued to Woehr et al. A safety IV catheter is described including a resilient needle guard which protects the needle tip upon removal of the needle from the catheter hub. The needle guard includes an arm that includes an opening through which a needle passes causing axial movement of the arm. This axial movement forces the arm into a groove or behind a rib located on the inside of the catheter hub, capturing the needle guard in the catheter hub. A potential issue with this design develops when the needle guard is not properly seated into the catheter hub. If the distal end of the needle guard arm is not in alignment with the groove in the catheter hub, excessive forces are placed on the needle causing a high drag force as the clinician removes the needle. And, since the needle guard arm is not properly seated in the groove, it may prematurely release from the catheter hub upon the removal of the needle leaving the needle tip exposed.

The prior art safety catheters all exhibit one or more drawbacks that have thus far limited their usefulness and full acceptance by health-care workers. What is needed therefore is a safety IV catheter that functions reliably, is easy and inexpensive to manufacture, and easy to use.

SUMMARY OF THE INVENTION

In accordance with the present invention there is provided a catheter introducer assembly. The catheter introducer assembly comprises a needle assembly having a needle attached to a needle hub and a distal end extending therefrom. The needle includes a bent area disposed between its proximal and distal ends. The catheter introducer assembly further includes a catheter assembly having a tubular catheter with a proximal end attached to a catheter hub. The needle is coaxially received within the catheter. The catheter introducer assembly further includes a needle tip protector disposed within the catheter hub. The needle tip protector is slidably disposed onto the needle, whereby when the needle is proximally removed from the catheter the protector remains attached to the needle.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 2 is an exploded perspective view of the catheter assembly and needle assembly including the needle tip protector of the present invention;

FIG. 3 is a perspective view of the needle tip protector of the present invention;

FIG. 4 is an elevation view of FIG. 3 taken along line 4—4 illustrating the hole positions in the rear flanges of the needle tip protector as manufactured;

FIG. 9 is a perspective view of the needle tip protector shown as removed from the catheter hub and illustrating the needle tip covered by the protector;

FIG. 10 is a perspective view of an alternate embodiment of the needle tip protector of the present invention.

DETAILED DESCRIPTION OF THE INVENTION

As used herein, the term "proximal" refers to a location on the catheter and needle assembly with needle tip protector closest to the clinician using the device and thus furthest from the patient on which the device is used. Conversely, the term "distal" refers to a location farthest from the clinician and closest to the patient.

Figure 1:
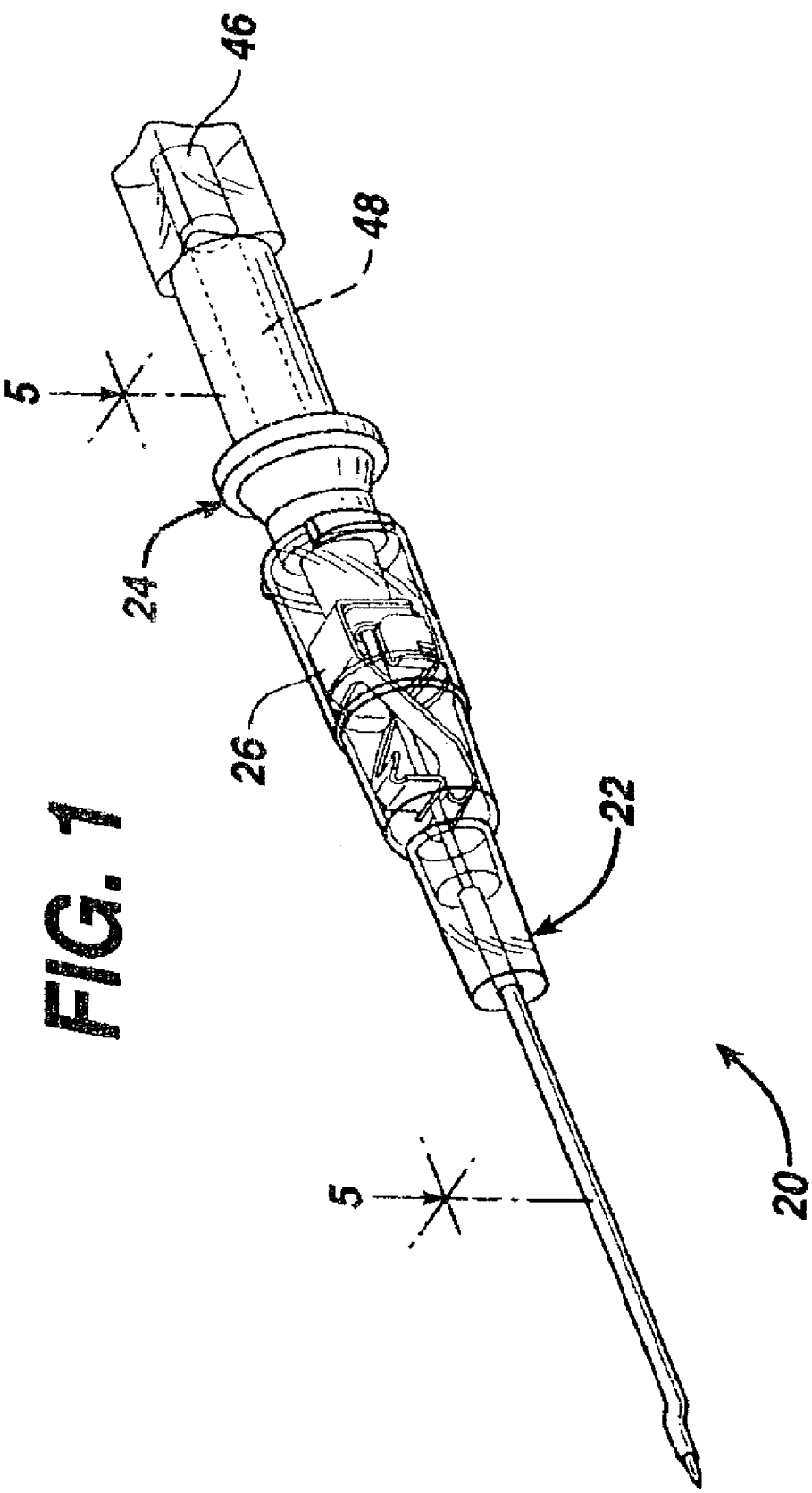
FIG. 1 is a perspective view of the catheter and needle assembly of the present invention.
Figure 5:
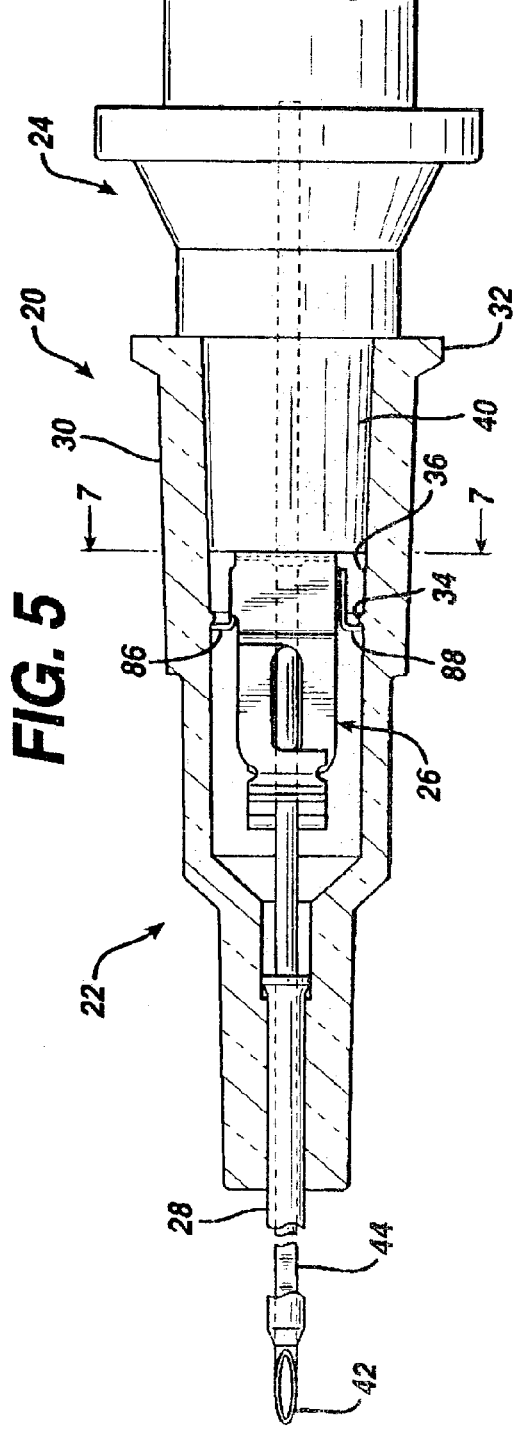
FIG. 5 is a section view of the catheter assembly and needle assembly taken along line 5—5 of FIG. 1.
Figure 6:
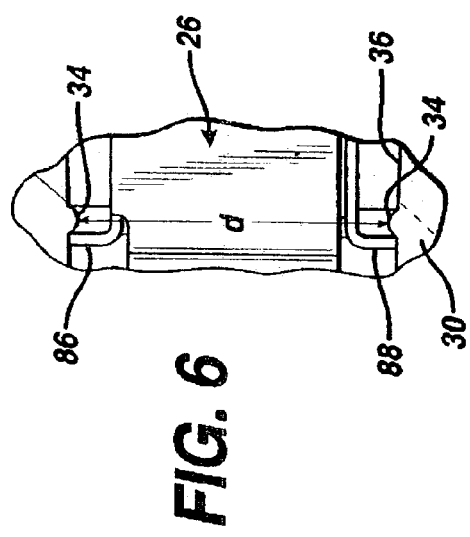
FIG. 6 is an enlarged partial section view of FIG. 5 illustrating the relative position of the needle tip protector tab and catheter hub rib.

As illustrated in FIGS. 1 and 2, IV catheter assembly 20 comprises catheter assembly 22 and needle assembly 24. Needle assembly 24 further includes needle tip protector 26. Catheter assembly 22 includes catheter 28 which is a tubular structure having a proximal end 31 and distal end 29. Proximal end 31 of catheter 28 is fixedly attached to catheter hub 30. Catheters are well known in the medical art and one of many suitable materials, most of which are flexible thermoplastics, may be selected for use in catheter 28. Such materials may include, for example, polyurethane or fluorinated ethylene propylene. Catheter hub 30 is a generally tubular structure having an internal cavity in fluid communication with the internal lumen of catheter 28. Catheter hub 30 may be made from a suitable, rigid medical grade thermoplastic such as, for example, polypropylene or polycarbonate. For illustration purposes catheter hub 30 is shown translucent, though in actual use it may be translucent or opaque. At the proximal end of catheter hub 30 is integrally attached Luer fitting 32, commonly known in the medical art. Luer fitting 32 provides for secure, leakproof attachment of tubing, syringes, or any of many other medical devices used to infuse or withdraw fluids through the catheter assembly. As is more clearly illustrated in FIGS. 5 and 6, rib 34 is a raised annular ring integral to and extending from internal sidewall 36 of catheter hub 30. Rib 34 is located approximately mid way between the proximal end and distal end of sidewall 36. Rib 34 plays an important role in securing needle tip protector 26 in catheter hub 30, as will be described in more detail later.

Referring again to FIGS. 1 and 2, needle assembly 24 comprises needle 38, which is a tubular structure with a proximal end 39 and distal end 41, needle hub 40, and needle tip protector 26. Needle tip protector 26 is assembled slidably on needle 38. Needle 38 is preferably made of stainless steel. Proximal end 39 of needle 38 is fixedly attached to needle hub 40. A bevel 42 is located at the most distal end of needle 38 creating a sharp piercing tip. Needle bend 44 is located at the distal end of needle 38 proximal to bevel 42 and is curve in needle 38. Needle bend 44 can be created by bending method such as "rotary draw bending." Rotary draw bending is a process well known in the metal bending art and involves using a clamp die and a bend die, which are molded to match the nominal diameter of needle 38, to rotate needle 38 against a pressure die. A mandrel is inserted into needle 38 during the procedure to minimize the stretching that occurs along the outer radius of needle 38, while a wiper die reduces wrinkling along the inner radius of needle 38. Bend 44 is formed at an angle away from second flange hole 72 in needle tip protector 26 and is important in preventing the complete removal of needle tip protector 26 from needle 38, as will be described in more detail later. In the preferred embodiment the angle of bend 44 is 45 to 90 degrees away from second flange hole 72.

Needle hub 40 is generally a tubular structure having an internal cavity in fluid communication with the lumen in needle 38. It is preferably made of a translucent or transparent generally rigid thermoplastic material such as, for example, polycarbonate. At the most proximal end of the internal cavity in needle hub 40 is fixedly attached porous plug 46. A flashback chamber 48 is created in the cavity distal to porous plug 46. Porous plug 46 contains a plurality of microscopic openings which are large enough to permit the passage of air and other gasses but small enough to prevent the passage of blood. Flashback chamber 48 fills with blood upon successful entry of the needle tip into the targeted vein, providing the clinician visual conformation of the correct placement of the needle.

Referring now to FIGS. 3 and 4, needle tip protector 26 has a proximal end 49 and distal end 50 and is preferably a unitary structure formed from a single piece of thin, resilient material, preferably stainless steel. First flange 66 and second flange 68 are generally square and are integrally connected at right angles to first outer wall 74 and second outer wall 76, respectively. First outer wall 74 is connected at a right angle to first tab flange 78. First tab flange 78 and second tab flange 80 are each formed at angles slightly greater than 90 degrees to second outer wall 76 so that the resulting dimension c is slightly larger than inside diameter d (see FIGS. 5–7) across rib 34 in catheter hub 30. In the preferred embodiment angles a and b are each approximately 94.25 degrees. In the preferred embodiment dimension c is approximately 0.005–0.009 inches larger than dimension d. First flange hole 70 is located in the center of first flange 66 and is over-sized to slidably receive needle 38. Second flange hole 72 and skirt 82 are located in the center of second flange 68. Skirt 82 is integral to second flange hole 72 and is formed by extruding material from second flange hole 72 in a direction distal to second flange 68. This permits for a very close but slidably fit over the nominal diameter of needle 38. Skirt 82 also functions to help maintain alignment of needle 38 to the center axis of needle tip protector 26. As would be understood by one skilled in the art, flange hole 72 would be appropriately sized to the particular needle "gauge" size to which it is designed to receive. First tab 86 and second tab 88 are connected at right angles to first tab flange 78 and second tab flange 80, respectively, and protrude outward away from the center axis of needle tip protector 26. First tab edge 90, located on the outer portion of first tab 86, and second tab edge 92, located on the outer portion of second tab 88, are each arcuate to approximately match the curve of sidewall 36 in catheter hub 30.

Referring again to FIG. 3, first beam 96 extends distally from first outer wall 74 and is angled toward and extends past the center axis of needle tip protector 26. At the distal end of first beam 96 is integrally formed curved first lip 98 which extends across and through the center axis of needle tip protector 26. Second beam 100 extends distally from second outer wall 76 and is angled toward and extends past the center axis of needle tip protector 26. At the distal end of second beam 100 is stop flange 102 which extends across and normal to the center axis of needle tip protector 26. At the end of stop flange 102 opposite its connection to second beam 100 is integrally formed curved second lip 104.

Figure 8:
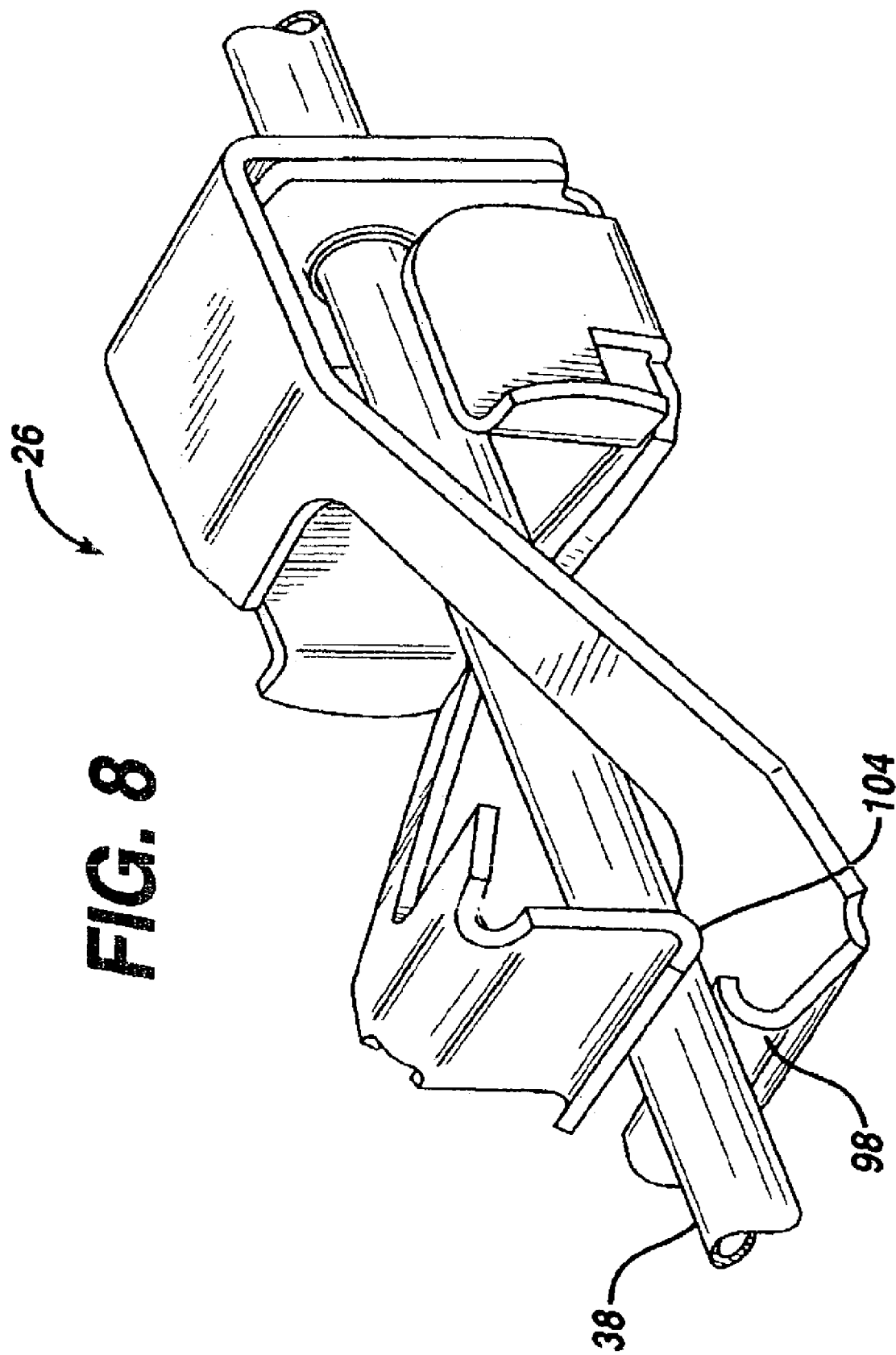
FIG. 8 is a perspective view of the needle tip protector shown as installed in the catheter hub with the needle inserted therethrough.

Referring now to FIGS. 5–9, needle tip protector 26 is assembled to needle 38 as follows;

The proximal end of needle 38 is fixedly attached to the distal end of needle hub 40, which contains porous plug 46 fixedly attached to its proximal end;

The distal end of needle 38 is inserted through first flange hole 70 and then through second flange hole 72 in needle tip protector 26, moving from proximal to distal;

First beam 96 and second beam 100 are flexed, as a result of their resilient properties, normal to the center axis of needle tip protector 26 so that needle 38 will pass between first lip 98 and second lip 104 (see FIG. 8);

Needle bend 44 is added to the distal end of needle 38 just proximal to bevel 42. Bend 44 is angled away from second flange hole 72 locally (see FIG. 9) thus preventing the complete removal of needle tip protector 26 from the distal end of needle 38.

Now needle assembly 24, including needle tip protector 26, is assembled into catheter assembly 22 as follows;

The distal end of needle 38 is positioned into the proximal end of catheter hub 30 and needle assembly 24 is moved distally causing needle 38 to enter catheter 28;

As needle assembly 24 continues to move distally, needle tip protector 26 enters the opening in the proximal end of catheter hub 30;

Continued distal movement of needle assembly 24 causes the distal edge of needle hub 40 to push first tab 86 and second tab 88 on needle tip protector 26 into contact with rib 34 located on hub sidewall 36;

Continued distal movement forces first tab 86 and second tab 88, due to the resilient properties of needle tip protector 26, past rib 34 and in contact with sidewall 36, just distal to rib 34.

Needle tip protector 26 is thus held distal to rib 34 inside the cavity in catheter hub 30 by the flexural forces of first tab 86 and second tab 88 since dimension c on needle tip protector 26 is larger than dimension d across rib 34 inside catheter hub 30. (see FIG. 6).

Figure 7:
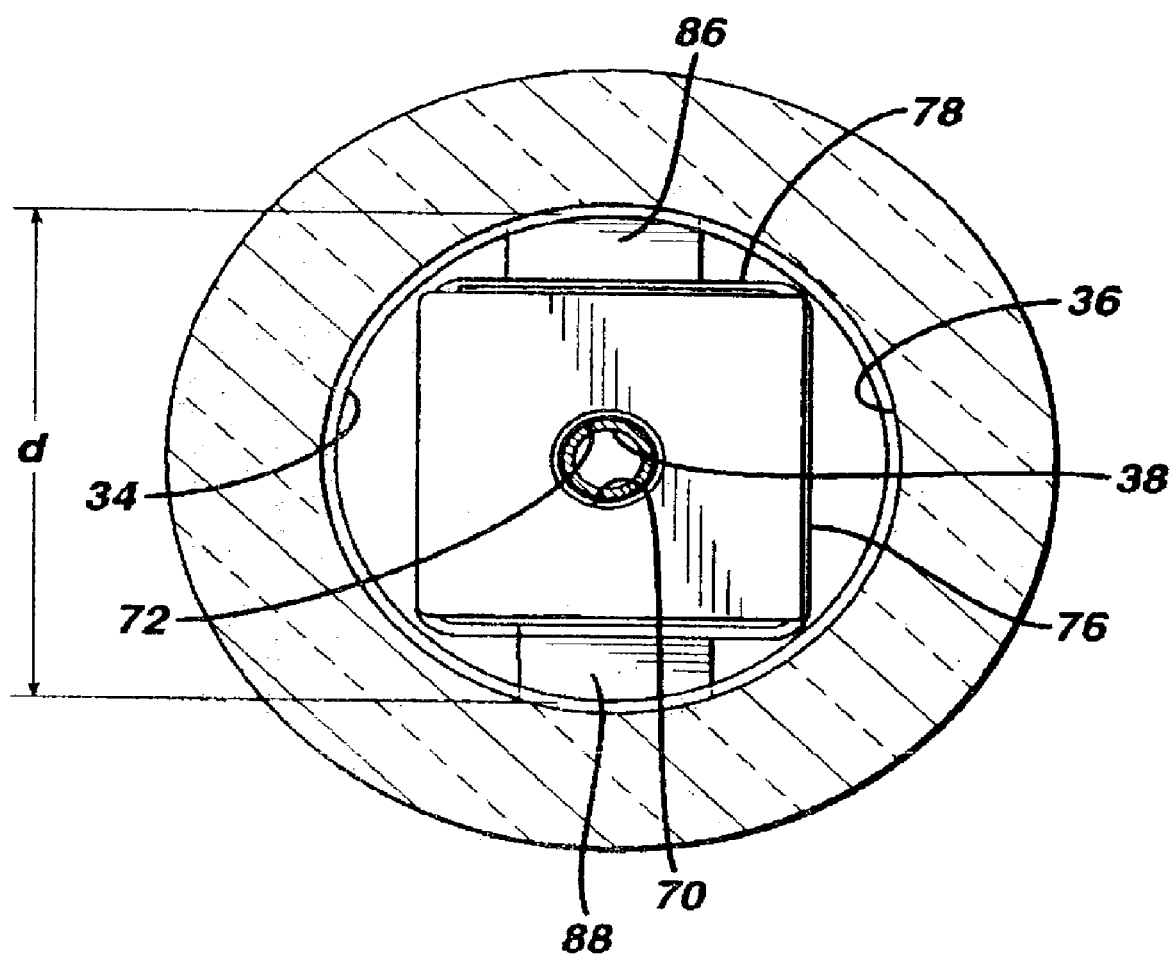
FIG. 7 is a section view of the catheter hub with needle tip protector installed taken along line 7—7 of FIG. 5.

As is best illustrated in FIG. 7, the movement of first tab 86 and second tab 88 as needle tip protector 26 is finally seated distal to rib 34 causes flexure in second outer wall 76 and first tab flange 78 resulting in the approximate alignment of first flange hole 70 and second flange hole 72.

Now, in actual clinical use, the IV catheter assembly 20 of the present invention functions as follows;

The distal end of needle 38, which extends just past the distal end of catheter 28 is inserted into the patient's vein;

The clinician observes blood in the flash chamber in needle hub 40;

The clinician grasps needle hub 40, and catheter assembly 22 alone is moved distally into the vein;

The clinician applies slight pressure to the insertion site to hold catheter assembly 22 secure;

The clinician grasps the needle hub and begins withdrawal of needle assembly 24 from catheter assembly 22. During this process, needle tip protector 26 remains secure inside catheter hub 30 until bend 44 on the distal end of needle 38 comes into contact with second flange hole 72. Just before bend 44 encounters second flange hole 72, the biasing forces of first beam 96 and second beam 100 cause stop flange 102 and first lip 98 to move normal to and across the center axis of needle 38, blocking any further distal movement of needle 38 relative to needle tip protector 26. After stop flange 102 and first lip 98 move normal to and across the center axis of needle 38, first beam 96 and second beam 100 prevent axial movement of needle 38 preventing needle 38 from being twisted enabling bend 44 to be manipulated through second flange hole 72;

Since bend 44 is angled away from second flange hole 72 and first beam 96 and second beam 100 prevent axial movement of needle 38 securing bend 44 from being manipulated through second flange hole 72, continued proximal movement of needle 38 carries needle tip protector 26 proximal as well, forcing first tab 86 and second tab 88 on needle tip protector 26 against rib 34. First tab 86 and second tab 88 are forced to flex normal to and toward the center axis of needle tip protector 26, permitting continued movement proximal, past rib 34;

Needle assembly 24 is now removed entirely from catheter assembly 22, with the needle tip covered by needle tip protector 26 of the present invention.

FIG. 10 shows an alternate embodiment of the present invention. In this embodiment, needle 138, similar to needle 38, includes sleeve 199. Sleeve 199 can be slidably or fixedly attached on needle 138 proximal to bend 144 such that sleeve 199 is biased against second flange hole 172 when needle 138 is removed from catheter assembly 22. Sleeve 199 helps prevent needle tip protector 126 from being completely removed from needle 138 by ensuring that bend 144 can not be manipulated through second flange hole 172.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims. In addition, it should be understood that every structure described above has a function and such structure can be referred to as a means for performing that function.

What is claimed is:

1. A catheter introducer assembly, comprising:
   a) a needle assembly comprising a needle having a diameter, a proximal end, attached to a needle hub, a distal end extending therefrom, said distal end including a sharp tip with a bevel, and a longitudinal axis therebetween, said needle further including a bent area disposed between said proximal and distal ends such that a portion of said needle distal of said bent area extends along a path other than said longitudinal axis and no portion of said bevel is in said bent area, said bevel extending at an angle relative to said longitudinal axis;
   b) a catheter assembly comprising a tubular catheter having a proximal end attached to a catheter hub, and a distal end, said introducer needle being coaxially received within said catheter;
   c) a needle tip protector disposed within said catheter hub, said needle tip protector is slidably disposed onto said needle, whereby when said needle is proximally removed from said catheter said protector remains attached to said needle.

2. The catheter introducer assembly of claim 1 wherein said bent area on said needle is angled 45–90 degrees away from its original direction.

3. The catheter introducer assembly of claim 1 wherein said needle diameter is constant between its distal and proximal ends.

4. The catheter introducer assembly of claim 1 further comprising a sleeve on said needle.

5. The catheter introducer assembly of claim 4 wherein said sleeve is attached proximal to said bent area to help secure said needle in said protector when said needle is removed from said catheter.

6. A catheter introducer assembly, comprising:
   a) a needle assembly comprising a hollow needle having an outer diameter, a proximal end, attached to a needle hub, a distal end extending therefrom, and a longitudinal axis therebetween, said needle further including a bent area disposed between said proximal and distal ends such that a longitudinal axis of said distal end of said needle is off set from, but generally parallel to, a longitudinal axis of said proximal end of said needle;

b) a catheter assembly comprising a tubular catheter having a proximal end attached to a catheter hub, and a distal end, said introducer needle being coaxially received within said catheter;

c) a needle tip protector disposed within said catheter hub, said needle tip protector is slidably disposed about said needle such that when said needle is proximally removed from said catheter said bent area prevents said needle tip protector from sliding off said needle so that said needle tip protector remains attached to said needle.

7. The catheter introducer assembly of claim 6 wherein said bent area on said needle is angled 45–90 degrees away from its original direction.

8. The catheter introducer assembly of claim 6 wherein said needle further comprising a sleeve on said needle.

9. The catheter introducer assembly of claim 8 wherein said sleeve is attached proximal to said bent area to help secure said needle in said protector when said needle is removed from said catheter.

10. A catheter introducer assembly, comprising:
a) a needle assembly comprising a hollow needle having a proximal end, attached to a needle hub, a distal end extending therefrom, and a longitudinal axis therebetween and a constant outer diameter between said distal and proximal ends, said needle further including a bent area disposed between said proximal and distal ends such that a longitudinal axis of said distal end of said needle is off set from, but generally parallel to, a longitudinal axis of said proximal end of said needle;

b) a catheter assembly comprising a tubular catheter having a proximal end attached to a catheter hub, and a distal end, said introducer needle being coaxially received within said catheter;

c) a needle tip protector disposed within said catheter hub, said needle tip protector is slidably disposed about said needle such that when said needle is proximally removed from said catheter said bent area prevents said needle tip protector from sliding off said needle so that said needle tip protector remains attached to said needle.

11. The catheter introducer assembly of claim 10 wherein said bent area on said needle is angled 45–90 degrees away from its original direction.

12. The catheter introducer assembly of claim 10 wherein said needle further comprising a sleeve on said needle.

13. The catheter introducer assembly of claim 12 wherein said sleeve is attached proximal to said bent area to help secure said needle in said protector when said needle is removed from said catheter.

14. The catheter introducer assembly of claim 1, said path of said needle portion distal of said bent area being offset from, but generally parallel to, said longitudinal axis.

* * * * *